United States Patent [19]

Hicks

[11] Patent Number: 4,780,449

[45] Date of Patent: Oct. 25, 1988

[54] CATALYST FOR THE CONVERSION OF METHANE

[75] Inventor: Robert F. Hicks, Huntington Beach, Calif.

[73] Assignee: W. R. Grace & Co.-Conn., New York, N.Y.

[21] Appl. No.: 943,873

[22] Filed: Dec. 19, 1986

Related U.S. Application Data

[63] Continuation of Ser. No. 745,453, Jun. 14, 1985, abandoned.

[51] Int. Cl.$^4$ .......................... B01J 23/02; B01J 23/10
[52] U.S. Cl. ...................................... 502/303; 502/302; 502/341; 502/344
[58] Field of Search ............... 502/302, 303, 341, 344; 585/500

[56] References Cited

U.S. PATENT DOCUMENTS 4,318,827  3/1982  Antos .................................... 502/303
4,381,991  5/1983  Bertolachini et al. .......... 502/400 X

FOREIGN PATENT DOCUMENTS 1250941  10/1971  United Kingdom .

OTHER PUBLICATIONS

Fekhretdinov et al., "Ceramic Material", Otkrytiya Izobret., Prom. Obraztsy, Tovarnye Znaki, 54(11), p. 72, (1977), [Chemical Abstracts, vol. 86, 175916f, (1977)].

Lundsford et al., "Evidence for the Formation of Gas Phase Radicals at Surfaces", Symposium of the New Surface Science on Catalysis Presented Before the Division of Colloid and Surface Chemistry, and the Division of Petroleum Chemistry, Inc., Philadelphia Meeting, Aug. 26–31, 1984.

*Primary Examiner*—W. J. Shine
*Attorney, Agent, or Firm*—Edward J. Cabic

[57] ABSTRACT

A process and catalyst for the synthesis of hydrogen, ethylene, ethane, and higher hydrocarbons from methane in the presence of oxygen is disclosed. The catalyst comprises metal oxides selected from a Group IIA metal, a Group IIIA metal, a lanthanide series metal excluding Ce, or mixtures thereof and optionally a promoter metal oxide selected from a Group IA metal, a Group IIA metal, a Group IIIA metal, a lanthanide series metal, a Group IVB metal, a Group VB metal, a Group IB metal, or mixtures thereof.

6 Claims, 2 Drawing Sheets

CATALYST FOR THE CONVERSION OF METHANE

This is a continuation of application Ser. No. 745,453, filed June 14, 1985, now abandoned.

BACKGROUND OF THE INVENTION

1. Field of the Invention

This invention relates to a process and catalyst for converting methane in the presence of oxygen into hydrogen and higher hydrocarbons which include ethane and ethylene.

2. Description of the Previously Published Art

Methane is a plentiful hydrocarbon feedstock which is obtained principally from natural gas. The methane content of natural gas can vary from 60% to 99%, the other components being ethane, propane, butane, carbon dioxide, and nitrogen. World reserves are estimated to be about $2.5 \times 10^{12}$ ft$^{-1}$. The production of chemicals from methane, however, is hampered by the lack of catalytic processes capable of activating methane towards chemical transformations. Today methane can be either combusted for its heating value, or steam reformed over iron or nickel catalysts to produce CO and $H_2$. The CO and $H_2$ are further reacted with $N_2$ to produce methanol and ammonia. As yet no attractive processes exist to convert methane directly into higher valued hydrocarbons, such as ethylene or propylene, which can then be used to produce liquid fuels, plastics, fibers, solvents, and a myriad of other organic compounds used by the chemical process industry. As a consequence, methane is an underutilized natural resource.

U.S. Pat. Nos. 4,172,810, 4,205,194, and 4,239,658 disclose a novel catalyst and process for converting methane into a hydrocarbon product rich in ethylene and benzene. The essential components of the catalyst are (1) a group VIII noble metal having an atomic number of 45 or greater, nickel, or group Ib noble metal having an atomic number of 47 or greater, (2) a group VIa metal oxide which is capable of being reduced to a lower oxide, and (3) a group IIa metal selected from the group consisting of magnesium and strontium composited with a passivated, spinel-coated refractory support or calcium composited with a passivated, non-zinc containing spinel-coated refractory support. The process consists of contacting the catalyst with methane at elevated temperatures for a short period of time, and recovering the hydrocarbons which are produced. During the exposure to methane some of the metal oxides contained in the catalyst are reduced, and the surface of the catalyst becomes covered with coke, rendering it inactive. Before the methane can be readmitted to the reactor, the catalyst must be regenerated by contact with an oxygen or water containing gas at elevated temperature.

U.S. Pat. No. 4,450,310 discloses a process for the conversion of methane into olefins and hydrogen by passing methane in the absence of oxygen and in the absence of water over a catalyst at temperatures above 500° C. The catalyst is composed of mixed oxides from group IA of the periodic table, including Li, Na, K, Rb, and Cs, and group IIA of the periodic table, including Be, Mg, Ca, Sr, and Ba, and optionally a promoter metal selected from Cu, Re, W, Zr, and Rh. The improvement of this process over the one described previously is the reduced amount of coke deposited on the catalyst during reaction, which presumably allows the reaction to proceed for a longer period of time before the catalyst must be regenerated.

G. E. Keller and M. M. Bhasin in J. Catal. 73, 9 (1982) disclose a process to produce ethylene and ethane from methane whereby pure methane is fed over a catalyst at atmospheric pressure and temperatures of 500° to 1000° C. As the methane is passed through the reactor it reacts with the metal oxide catalyst producing ethane and ethylene, while simultaneously reducing the metal oxide. After a short exposure to methane, the catalyst must be regenerated, and the feed is switched to pure oxygen which reoxidizes the metal oxide. All catalysts were prepared by supporting a metal oxide on $Al_2O_3$. Active catalysts are supported oxides of Sn, Pb, Sb, Bi, Tl, Cd, and Mn. The authors suggest that the ability of these oxides to cycle between two oxidation states is essential for having good activity and selectivity for the conversion of methane into $C_2$ hydrocarbon products.

Jones, Leonard, and Sofranko issued a series of patents which disclose a process similar to that of Keller and Bhasin for producing ethane and ethylene from methane. The reaction is carried out at atmospheric pressure, temperatures of 500° to 1000° C, and the methane and oxygen are fed separately in a cyclic fashion. The improvements of the Jones process over the Keller process appear to be: (1) the use of a fluidized-bed catalytic reactor, instead of a fixed-bed catalytic reactor, and (2) supporting the active metal oxides on $SiO_2$, instead of $Al_2O_3$. Jones, Leonard, and Sofranko also suggest that "reducible" metal oxides must be used as catalysts for this process, and these are oxides of Sb, Mn, Ge, Pb, Sn, In, and Bi. These oxides are claimed in U.S. Pat. Nos. 4,443,644; 4,443,649; 4,443,645; 4,443,647; 4,444,984; 4,443,648; and 4,443,646, respectively. The reducible oxides can also be promoted with alkali metals (U.S. Pat. No. 4,499,322) or alkaline earth metals (U.S. Pat. No. 4,495,374) and stability is enhanced by the presence of phosphorus (PCT Published Application WO 85/00804). Other related work includes Ru promoted by alkali and alkaline earth metals (U.S. Pat. No. 4,489,215), and the use of reducible rare earth oxides, $CeO_2$ (U.S. Pat. No. 4,499,324) and $Pr_6O_{11}$ (U.S. Pat. No. 4,499,323).

Hinsen and Baerns (German Patent No. 3,237,079, Chem.-Ztg. 107, 223 (1983) and Proc. 8th Intl. Cong. Catal. 3, 581 (1984)) disclose a new process for the synthesis of ethylene and ethane from methane. The improvement of this process over previous processes is that methane and oxygen are fed simultaneously to the catalytic reactor, thereby obviating the need to cycle between reaction and catalyst regeneration. The preferred method of adding the oxygen is either laterally along the length of the reactor, or to a large recirculating stream of the hydrocarbon gas. These methods of oxygen addition insure that the oxygen partial pressure is kept low, so as to maximize selectivity. Good selectivities are observed at reaction temperatures of 650° to 750° C. and at low $O_2$ partial pressures ($P_{O2}=0.05$ to 0.10 atm) relative to methane ($P_{CH4}=0.25$ to 0.50 atm). For the continuous feeding case, Baerns found that reducible oxides of Pb, Sb, Sn, Bi, Cd, Tl, and In are active and selective catalysts. Reducing the acidity of the support is also essential for maintaining good selectivity, and this can be achieved by using $SiO_2$ support instead of $TiO_2$, $SiO_2/Al_2O_3$, or $Al_2O_3$, by increasing the PbO weight loading above 10.0%, and by promoting the catalyst with alkali.

U.S. Pat. No. 2,020,671 discloses the production of oxygenated organic compounds by reaction of methane with steam at temperatures of 200°–700° C. in the presence of catalysts selected from metal salts of the alkaline earth metals, aluminum, magnesium, and zinc.

U.S. Pat. No. 2,859,258 discloses the production of ethylene from methane in the presence of oxygen containing metal compound wherein the metal is selected from the second, third, and fourth groups of the periodic table, such as aluminum oxide, magnesium aluminum silicate, and magnesium aluminum molybdate.

3. Objects of the Invention

It is an object of this invention to obtain a catalytic process to convert methane in the presence of oxygen to hydrogen, ethylene, ethane, and higher hydrocarbons with high selectivities and high methane conversion per pass.

It is a further object of this invention to develop an active and selective catalyst for the synthesis of hydrogen, ethylene, ethane, and higher hydrocarbons from methane in the presence of oxygen.

It is a further object of this invention to operate the process with simultaneous addition of methane and oxygen to the catalytic reactor, so as to avoid intermittent regeneration of the catalyst, thereby obtaining a continuous synthesis of hydrogen, ethylene, ethane, and higher hydrocarbons from methane.

These and further objects will become apparent as the description of the invention proceeds.

SUMMARY OF THE INVENTION

It has been found that methane can be converted into hydrogen, ethylene, ethane, and higher hydrocarbon products by contacting a gas containing methane and oxygen with a metal oxide of Group IIA metals of the Periodic Table such as Be, Mg, Ca, Sr, and Ba; a metal oxide of Group IIIA metals of the Periodic Table, such as Sc, Y, and La; a metal oxide of the lanthanide series excluding Ce, such as Pr, Nd, Sm, Eu, Gd, Tb, Dy, Ho, Er, Tm, Yb, and Lu; and mixtures thereof. The Periodic Table being refered to is the one approved by IUPAC. The catalytic reaction is preferably carried out at temperatures between 500° and 1000° C. and pressures between 1 and 25 atmospheres. Some water, CO, and $CO_2$ is also produced as a byproduct of the reaction.

The present process is distinguished from previous known processes for the synthesis of hydrocarbons from methane in the presence of oxygen by the use of metal oxides which are not reducible, such as MgO, SrO, $Y_2O_3$, and $La_2O_3$. A second feature of these catalysts is that they are basic and ionic metal oxides. Thus, metal oxides which exhibit basic character, and do not have a redox potential, are generally selective catalysts for synthesizing higher hydrocarbons from a mixture of methane and oxygen.

It has further been found that the metal oxides of Group IIA, IIIA, and the lanthanide series excluding Ce and mixtures thereof can be improved by the addition of one or more promoter oxides selected from the following metals:

(a) metals of Group IA, which are Li, Na, and K;
(b) metals of Group IIA, which are Be, Mg, Ca, Sr, and Ba;
(c) metals of Group IIIA, which are Sc, Y, and La;
(d) metals of the lanthanide series, which are Ce, Pr, Nd, Sm, Eu, Gd, Tb, Dy, Ho, Er, Tm, Yb, and Lu;
(e) metals of Group IVB, which are Sn and Pb;
(f) metals of Group VB, which are Sb and Bi; and
(g) metals of Group IB, which are Cu, Ag, and Au, and
(h) mixtures thereof.

The promoter oxide can be added by a variety of techniques. The loading of the promoter can vary from a catalytically effective amount up to 50 wt %, and preferably up to 10 wt %.

Preferred catalysts according to this invention include (a) a catalyst wherein the base metal oxide is $Y_2O_3$ and the promoter oxide is $Li_2O$, BeO, MgO, CaO, SrO, BaO, tin oxide, lead oxide, antimony oxide, bismuth oxide, copper oxide, silver oxide, or gold oxide;

(b) a catalyst wherein the base metal oxide is $La_2O_3$ and the promoter oxide is $Li_2O$, BeO, MgO, CaO, SrO, BaO, tin oxide, lead oxide, antimony oxide, bismuth oxide, copper oxide, silver oxide, or gold oxide; and (c) a catalyst wherein the base metal oxide is in the form of a mixture of rare earth oxides, as is formed in rare earth minerals, but with a portion of the $CeO_2$ removed, and the promoter oxide is $Li_2O$, BeO, MgO, CaO, SrO, BaO, tin oxide, lead oxide, antimony oxide, bismuth oxide, copper oxide, silver oxide, or gold oxide.

The present process is also distinguished from previous known processes for the synthesis of hydrocarbons from methane in that an inert support material for the active metal oxide is not necessary, and in some cases may be deleterious to the overall performance of the catalyst.

The present process is further distinguished from previous known processes for the synthesis of hydrocarbons from methane by feeding methane and oxygen simultaneously to the catalytic reactor. By using the catalysts described herein, the synthesis of hydrocarbons from methane can be carried out in the presence of oxygen without reducing the yield of hydrocarbon product. Such a simultaneous and continuous feeding of a methane and oxygen mixture to the catalytic reactor eliminates the need for periodic catalyst regeneration, and it is the preferred mode of operation of the present invention.

This invention is further described in the following description of its preferred embodiments.

DESCRIPTION OF THE PREFERRED EMBODIMENTS

Figure 1:
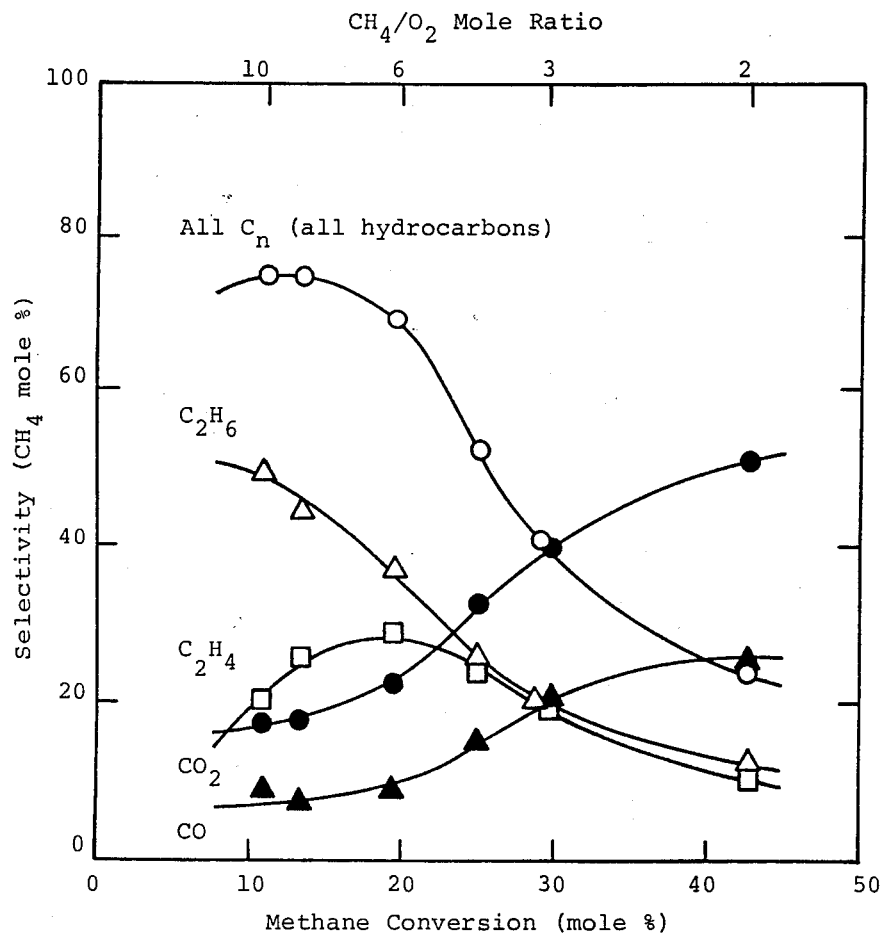
FIG. 1 is a graph illustrating the dependence of product selectivity (based on moles of methane converted) upon methane conversion.

The catalyst can be composed of one or more base metal oxides of Group IIA, Group IIIA, and the lanthanide series. These materials can be supplied as metal oxides, or as metal salts which are subsequently decomposed to the oxide form. Some examples of suitable metal salts are acetate, acetylacetonate, carbide, carbonate, hydroxide, formate, oxalate, nitrate, phosphate, sulfate, sulfide, tartrate, and halides such as fluoride, chloride, bromide, and iodide.

Particularly suitable catalysts for the process described herein are the rare earth oxides which include $La_2O_3$, $Y_2O_3$, $Pr_6O_1$; $Nd_2O_3$, $Sm_2O_3$, $Eu_2O_3$, $Gd_2O_3$, $TbO_2$, $Dy_2O_3$, $Ho_2O_3$, $Er_2O_3$, $Tm_2O_3$, $Yb_2O_3$, and $Lu_2O_3$. These oxides may be used in their pure form, or as a mixture such as is commonly obtained from mineral deposits. If a mixture obtained from an ore is used, for example, bastnasite or monazite is used, then it is necessary to reduce the cerium content of the ore to a low level. Cerium oxide is an acidic solid, and can readily cycle between the +3 and +4 oxidation state. Consequently, $CeO_2$ converts methane in the presence of oxygen into CO and $CO_2$, instead of ethylene, ethane, and higher hydrocarbons.

In another embodiment of the invention the catalyst can be composed of mixtures of the base metal oxides described above with promoter oxides, such as metal oxides of Groups IA, IIA, IIIA, IVB, VB, IB, and the lanthanide series. A preferred form of the catalyst is to deposit promoter amounts of elements of Groups IA, IIA, IVB, VB, or IB onto a rare earth oxide. Another preferred form of the catalyst is to deposit elements of Groups IA, IIIA, IVB, VB, IB, or the lanthanide series onto an alkaline earth oxide.

The elements of Groups IA, IIA, IVB, VB, or IB can be deposited onto a rare earth oxide by a variety of techniques. The same techniques apply for depositing elements of Groups IA, IIIA, IVB, VB, IB, or the lanthanide series onto an alkaline earth oxide. Suitable techniques are adsorption, incipient-wetness impregnation, precipitation, coprecipitation, and dry-mixing. After depositing the element from one of the groups listed above, it is converted into the oxide form by treating in an atmosphere of oxygen at elevated temperatures. The weight loading of the promoter metal oxide deposit can vary between 0% and 50%, but preferably less than 10%.

The metal oxides described above can also be deposited on conventional supports, such as $SiO_2$ and $Al_2O_3$. These supports are not an essential part of the catalyst formulation, but may be used to give the catalyst pellet improved shape and/or improved mechanical strength and durability. If conventional supports are used, it is important that their acidity be reduced, otherwise the supports may catalyze the formation of carbon oxides from methane and oxygen. The support acidity can be reduced by a number of means, such as using a high weight loading of the active metal oxide, doping the support with alkali metal prior to depositing the metal oxide, or using supports of low porosity.

A suitable method of preparing an unsupported catalyst is to deposit a promoter metal salt, such as from Groups IA or IIA, onto a rare earth oxide by incipient-wetness impregnation. The metal salt may be dissolved in water or another solvent and then mixed with the rare earth oxide, thereby wetting the surface of the oxide. Aqueous solutions of the metal salt are desirable, and in this case, a water soluble salt is used. To facilitate dissolution of the metal salt, acids and/or bases can be added to the solution. After wetting the rare earth oxide with the salt solution, the oxide is dried in an oven. Finally, to prepare the solid for use in the process, it may be calcined at high temperature for a period of time to convert the metal or metal salts to the metal oxide form. For example, the catalyst may be placed in a kiln, or a tube through which air may be passed, and heated for several hours at an elevated temperature, which preferably is between about 500° and 1000° C.

The unsupported metal oxide used as the catalyst can be prepared in a variety of pellet shapes and sizes, the shape and size being dictated by the need to have good contact between the gas and the solid surface of the catalyst. The pellets can be prepared in the conventional manner using techniques well known to persons skilled in the art. For example, the catalyst pellet may be prepared by extrusion of a slurry of the metal oxide. Pellets formed in this manner are then dried and calcined at elevated temperatures. The addition of promoter metal oxides, such as from Groups IA or IIA of the Periodic Table, to the base metal oxide can be performed before or after the base metal oxide has been shaped into pellets.

The method of catalyst preparation is further illustrated in the examples given below.

The catalyst described above is charged to a reactor and contacted with a gas containing methane and oxygen at elevated temperatures. The hydrocarbon feedstock for this process is natural gas which contains methane, ethane, propane, and other light hydrocarbons. The methane content of the gas is between 60 to 100 volume percent, preferably 90 to 100 volume percent. The natural gas is mixed with a stream containing oxygen to give a hydrocarbon to oxygen ratio (by volume) of 1 to 50, preferably between 2 and 15. The stream containing oxygen may contain an inert diluent, such as nitrogen or argon. However, it is preferable that substantially pure oxygen be used, because the diluents require a larger reactor size and must be removed from the process stream to purify the product.

The optimum ratio of hydrocarbon to oxygen fed to the reactor is chosen such that the yield of ethylene, ethane, and higher hydrocarbons is a maximum. This choice is governed by a number of factors, such as the catalyst composition, the reaction temperature and pressure, and the desired distribution of hydrocarbon products. As the oxygen partial pressure is increased relative to the methane partial pressure, the conversion of methane in the reactor increases. However, the yield of ethylene and ethane does not increase proportionally, because at high oxygen partial pressures more carbon oxides are produced relative to the desired hydrocarbon products. This tradeoff is illustrated in FIG. 1 for the catalyst described in Example 18, using an integral fixed-bed reactor. In this figure, the selectivity (based on moles of methane converted) is cross-plotted against methane conversion and the methane to oxygen feed ratio. The combined selectivity to ethylene, ethane, and higher hydrocarbons is identified as All $C_n$ in the figure. These data were obtained at 700° C., 1 atm. pressure, a GHSV of $8 \times 10^5$ hr$^{-1}$ (NTP), and an $O_2$ feed of 10 vol %. Argon diluent was used in this experiment to maintain a constant space velocity.

Figure 2:
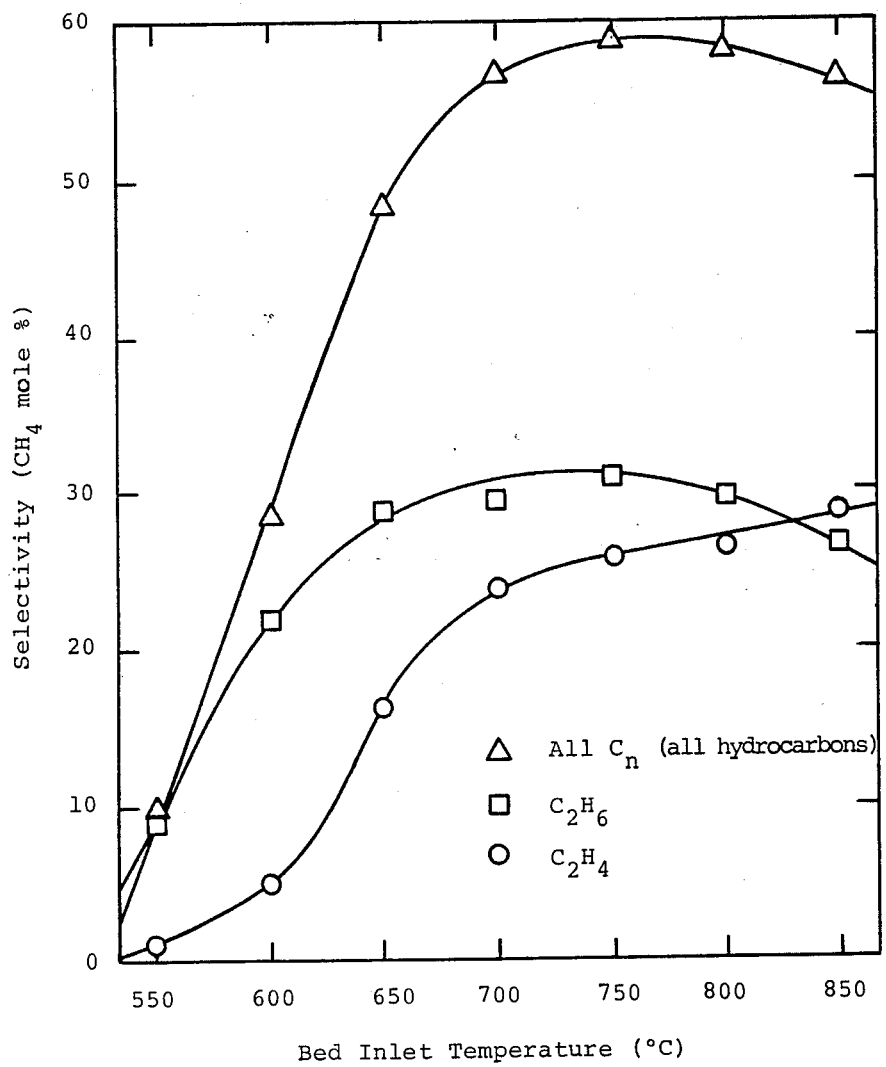
FIG. 2 is a graph illustrating the dependence of product selectivity upon operating temperature.

Operating temperatures for contacting the methane and oxygen with the catayyst are between 500° and 1000° C., preferably between 550° and 850° C. The optimum choice of reaction temperature depends on a number of factors, such as the composition of the catalyst, the partial pressures of hydrocarbon and oxidant, and the desired distribution of hydrocarbon products. The dependence of hydrocarbon selectivity upon operating temperature is shown in FIG. 2 for the catalyst described in Example 6. These data were obtained at a GHSV of 37,500 hr−1 (NTP), a methane partial pressure of 0.30 atm, an oxygen partial pressure of 0.05 atm, and an argon partial pressure of 0.65 atm. For all temperatures investigated in FIG. 2 the oxygen conversion was 100%. The data in FIG. 2 indicate that maximum selectivities to higher hydrocarbons are observed at temperatures between 650° and 850° C. The maximum selectivity to ethylene is observed at the highest temperature investigated, 850° C.

Operating pressures for contacting the methane and oxygen mixture with the catalyst are not critical. However, the total system pressure does effect the performance, since increasing the pressure tends to decrease the selectivity to higher hydrocarbons. The effect of system pressure varies depending on the composition of the catalyst used. Preferred operating pressures are between 1 and 50 atms., more preferably between 1 and 20 atms.

Several different contacting schemes can be used to maximize the conversion of methane to ethylene, ethane, and higher hydrocarbons in the catalytic reactor. In one preferred embodiment, the reactor contains a fixed-bed of catalyst, and the hydrocarbon and oxygen streams are mixed and fed to the reactor. In a second preferred embodiment, the reactor contains a fixed-bed of catalyst, the hydrocarbon feedstock is fed into one end of the reactor, and the oxygen is fed in at several inlets evenly spaced down the length of the reactor. Other contacting schemes can be used whereby the catalyst is suspended in a fluidized-bed, an ebullating-bed, a moving-bed, or an entrained-bed, although a fixed-bed of catalyst is particularly well suited to contacting the solid oxide with the gas containing methane and oxygen. Fixed-beds of catalyst can be operated in series or in parallel, depending on the desired yield and throughput of hydrocarbons required by the process.

In addition to producing ethylene, ethane, and higher hydrocarbons, the catalytic reaction also produces large amounts of hydrogen. This hydrogen is valuable as a fuel, as well as being a desirable reactant at a refinery where there are many hydrogen consuming reactions taking place.

Having described the basic aspects of the invention, the following examples are given to illustrate specific embodiments thereof. Conversions and selectivities reported in the examples are given on a per mole of methane basis.

EXAMPLES 1-11

These examples illustrate the preparation of pure oxide catalysts according to the present invention.

Pure metal oxides of Groups IIA and IIIA of the Periodic Table, and metal oxides of the lanthanide series were obtained and calcined at 900° C. in a kiln for 4 hours. These solids were then pressed into pellets, crushed, and sieved to a mesh size between 20 and 32. The oxides are listed in Table 1.

EXAMPLE 12

This example describes the test procedure for the evaluation of the catalysts and sets forth the results.

The pellets of metal oxide from Examples 1–11 were separately charged to a quartz tube (4 mm inside diameter) to give a catalyst bed depth of 25.4 mm. The quartz tube was then immersed in a fluidized sand-bath heater and brought up to reaction temperature over a 2 hr period under 50 cc/min of flowing argon. Once at reaction temperature, the feed was switched to a mixture of methane (0.30 atm), oxygen (0.05 atm), and argon (0.65 atm), and the flow rate was set at a GHSV (gas hourly space velocity) of 37,500 hr$^{-1}$ (NTP). Periodically, the effluent from the reactor was analyzed by on-line gas chromatography. The reactions were carried out from 4 to 12 hours, during which time little or no deactivation of the catalysts occurred. Results for several of the metal oxides tested are shown in Table 1. In these tests the reaction temperature was chosen to give the maximum yield of hydrocarbon products. The bed inlet temperature corresponding to this optimum is shown in Table 1. The combined selectivity to ethylene, ethane, and higher hydrocarbons is listed under All $C_n$ in the Table, and the last column gives the mole ratio of hydrogen to ethylene and ethane in the reactor effluent. Oxygen and carbon material balances were closed to within ±5%.

TABLE 1

ACTIVITY AND MAXIMUM SELECTIVITY OF PURE OXIDES FOR THE CONVERSION OF METHANE

| Example | Catalyst | T (°C.) | Selectivity (%) | | | | | Conversion (%) | | $H_2/(C_2H_4 + C_2H_6)$ |
| | | | $C_2H_4$ | $C_2H_6$ | All $C_n$ | CO | $CO_2$ | $O_2$ | $CH_4$ | |
| --- | --- | --- | --- | --- | --- | --- | --- | --- | --- | --- |
| 1 | MgO | 900 | 32.1 | 17.9 | 52.1 | 17.7 | 30.2 | 100 | 18.1 | 1.6 |
| 2 | CaO | 750 | 15.1 | 26.1 | 42.0 | 14.9 | 43.2 | 100 | 15.3 | 1.7 |
| 3 | SrO | 850 | 22.1 | 46.5 | 70.5 | 6.2 | 23.4 | 36 | 8.0 | 0.4 |
| 4 | $Sc_2O_3$ | 900 | 30.7 | 16.5 | 48.8 | 21.7 | 29.5 | 100 | 17.6 | 2.0 |
| 5 | $Y_2O_3$ | 800 | 26.8 | 27.4 | 56.2 | 12.5 | 31.0 | 100 | 18.0 | 1.0 |
| 6 | $La_2O_3$ | 750 | 25.7 | 30.9 | 59.1 | 8.1 | 32.8 | 100 | 19.6 | 1.1 |
| 7 | $Pr_6O_{11}$ | 850 | 8.7 | 16.6 | 25.6 | 8.0 | 66.4 | 100 | 11.3 | 1.6 |
| 8 | $Nd_2O_3$ | 750 | 22.5 | 31.5 | 57.0 | 7.2 | 35.8 | 100 | 17.9 | 0.9 |
| 9 | $Sm_2O_3$ | 750 | 23.5 | 29.5 | 55.8 | 10.5 | 33.7 | 100 | 17.9 | 1.0 |
| 10 | $Eu_2O_3$ | 700 | 24.4 | 28.2 | 55.9 | 9.8 | 34.3 | 100 | 18.2 | 1.2 |
| 11 | $Gd_2O_3$ | 800 | 31.1 | 27.2 | 61.0 | 9.6 | 29.4 | 100 | 19.2 | 1.1 |

From the data shown in Table 1, it is evident that all of the pure metal oxide catalysts exhibit high selectivities to ethylene, ethane, and higher hydrocarbons. It is also evident that a large amount of hydrogen is produced along with the hydrocarbons, such that the mole ratio of $H_2$ to $C_2H_4$ and $C_2H_6$ in the product varies between 0.4 and 1.7. This hydrogen can be used as a fuel, or in a refinery complex where there are many hydrogen consuming reactions taking place. Particularly high selectivities to hydrocarbon products are exhibited by MgO, SrO, $Y_2O_3$, $La_2O_3$, $Nd_2O_3$, $Sm_2O_3$, $Eu_2O_3$, and $Gd_2O_3$. Although the SrO catalyst exhibits the highest selectivity, this advantage is offset by the low oxygen and methane conversion per pass. Of the oxides listed, the rare earth oxides, including $Y_2O_3$, $La_2O_3$, $Nd_2O_3$, $Sm_2O_3$, $Eu_2O_3$, and $Gd_2O_3$, appear to offer the best overall performance characteristics, which are selectivities of approximately 60% to higher hydrocarbons, 100% $O_2$ conversion per pass, and a lower operating temperature (750°–800° C.) for achieving maximum hydrocarbon yield.

EXAMPLE 13

The experimental results for these catalyst samples are given in Tables 2 and 3.

TABLE 2
ACTIVITY AND MAXIMUM SELECTIVITY OF OXIDE MIXTURES CONTAINING $La_2O_3$ FOR THE CONVERSION OF METHANE

| | | | Selectivity (%) | | | | | Conversion (%) | | |
|---|---|---|---|---|---|---|---|---|---|---|
| Example | Catalyst | T (°C.) | $C_2H_4$ | $C_2H_6$ | All $C_n$ | CO | $CO_2$ | $O_2$ | $CH_4$ | $H_2/(C_2H_4 + C_2H_6)$ |
| 6 | $La_2O_3$ | 750 | 25.7 | 30.9 | 59.1 | 8.1 | 32.8 | 100 | 19.6 | 1.1 |
| 13 | $Li_2O/La_2O_3$ | 800 | 32.6 | 37.6 | 75.9 | 1.6 | 22.5 | 100 | 21.6 | 0.2 |
| 14 | $Na_2O/La_2O_3$ | 800 | 31.4 | 33.2 | 69.2 | 2.4 | 28.4 | 100 | 20.0 | 0.4 |
| 15 | $K_2O/La_2O_3$ | 800 | 30.1 | 30.3 | 64.0 | 7.7 | 28.3 | 100 | 20.6 | 0.8 |
| 16 | $MgO/La_2O_3$ | 750 | 28.0 | 32.1 | 65.4 | 8.5 | 26.1 | 100 | 20.7 | 0.7 |
| 17 | $CaO/La_2O_3$ | 750 | 28.6 | 31.1 | 64.3 | 9.4 | 26.3 | 100 | 19.4 | 0.8 |
| 18 | $SrO/La_2O_3$ | 750 | 28.7 | 34.9 | 69.0 | 4.8 | 26.2 | 100 | 20.9 | 0.6 |
| 19 | $BaO/La_2O_3$ | 800 | 30.5 | 33.6 | 68.2 | 3.2 | 28.7 | 100 | 20.3 | 0.5 |
| 20 | $PbO/La_2O_3$ | 750 | 24.9 | 33.2 | 60.6 | 3.5 | 35.9 | 100 | 18.5 | 0.5 |
| 21 | $Bi_2O_3/La_2O_3$ | 750 | 27.0 | 34.6 | 65.2 | 2.1 | 32.7 | 100 | 18.4 | 0.3 |
| 22 | $AgO/La_2O_3$ | 800 | 27.8 | 31.9 | 62.8 | 5.4 | 31.8 | 100 | 20.0 | 0.7 |

TABLE 3
ACTIVITY AND MAXIMUM SELECTIVITY OF OXIDE MIXTURES CONTAINING MgO FOR CONVERSION OF METHANE

| | | | Selectivity (%) | | | | | Conversion (%) | | |
|---|---|---|---|---|---|---|---|---|---|---|
| Example | Catalyst | T (°C.) | $C_2H_4$ | $C_2H_6$ | All $C_n$ | CO | $CO_2$ | $O_2$ | $CH_4$ | $H_2/(C_2H_4 + C_2H_6)$ |
| 1 | MgO | 900 | 32.1 | 17.9 | 52.1 | 17.7 | 30.2 | 100 | 18.1 | 1.6 |
| 23 | $Li_2O/MgO$ | 850 | 38.0 | 29.1 | 70.6 | 5.4 | 23.9 | 100 | 21.1 | 0.7 |
| 24 | $Na_2O/MgO$ | 800 | 27.5 | 31.6 | 61.4 | 6.8 | 31.8 | 100 | 19.4 | 0.9 |
| 25 | $K_2O/MgO$ | 900 | 37.5 | 18.6 | 59.3 | 11.7 | 29.0 | 100 | 19.3 | 1.1 |
| 26 | $Y_2O_3/MgO$ | 900 | 35.6 | 20.2 | 58.2 | 12.2 | 29.6 | 100 | 16.5 | 1.3 |
| 27 | $La_2O_3/MgO$ | 850 | 28.8 | 23.1 | 53.8 | 11.1 | 35.1 | 100 | 18.0 | 1.3 |
| 28 | $BaO/MgO$ | 850 | 27.6 | 28.5 | 57.8 | 8.3 | 33.9 | 100 | 17.4 | 0.9 |

This example illustrates the preparation of a mixture of oxide catalysts according to the present invention.

A solution of lithium salt was prepared by dissolving $LiNO_3$ in distilled water. Lanthanum oxide was then impregnated to incipient-wetness by the solution of $LiNO_3$. The mixture was dried in a vacuum oven at 110° C. for 12 hours. The dried solid was then calcined in air at 600° C. for 4 hours. Enough lithium was deposited on the $La_2O_3$ to give a finished loading of 1.0 wt% $Li_2O$.

EXAMPLES 14–28

These examples illustrate the preparation of additional mixtures of oxide catalysts according to the present invention.

Following the procedure of Example 13, catalysts were produced with 1.0 wt % of various metal oxides on either $La_2O_3$ or MgO. The catalysts prepared are listed in Tables 2 and 3.

EXAMPLE 29

This example describes the test procedure for the evaluation of the mixed oxide catalysts and sets forth the results.

Each of the catalysts of Examples 13–28 were separately pressed into pellets of mesh size between 20 and 32, charged to the quartz reactor, and exposed to the reaction conditions as described in Example 12 above.

Comparison of the data in Tables 2 and 3 indicates that the selectivity of the base metal oxide, in this case $La_2O_3$ or MgO, can be increased by impregnating them with other metal oxides of Groups IA, IIA, IIIA, VB, IVB, and IB of the Periodic Table. The especially preferred catalysts appear to be $La_2O_3$ promoted with alkali metal oxides, $La_2O_3$ promoted with alkaline earth oxides, and MgO promoted with $Li_2O$.

EXAMPLES 30–33

This example illustrates the use of different amounts of a promoter oxide on a base metal oxide.

Following the procedure of Example 13 and using $Sr(NO_3)_2$ instead of $LinO_3$, catalysts were produced with weight loadings of 0.25 to 10.0 wt % SrO on $La_2O_3$. The catalysts prepared are listed in Table 4.

EXAMPLE 34

This example describes the test procedure for the evaluation of the strontium oxide-promoted lanthanum oxide catalysts prepared in Examples 30–33, and sets forth the results.

Each of the catalysts of Examples 30–34 were separately pressed into pellets of mesh size between 20 and 32, charged to the quartz reactor, and exposed to the reaction conditions as described in Example 12 above. The experimental results for these catalyst samples are given in Table 4.

TABLE 4
ACTIVITY AND SELECTIVITY OF MIXTURES OF SrO AND $La_2O_3$ FOR THE CONVERSION OF METHANE AT 750° C.

| | | Selectivity (%) | | | | | Conversion (%) | | |
|---|---|---|---|---|---|---|---|---|---|
| Example | SrO (wt %) | $C_2H_4$ | $C_2H_6$ | All $C_n$ | CO | $CO_2$ | $O_2$ | $CH_4$ | $H_2/(C_2H_4 + C_2H_6)$ |
| 6 | 0.00 | 25.7 | 30.9 | 59.1 | 8.1 | 32.8 | 100 | 19.6 | 1.1 |
| 30 | 0.25 | 28.9 | 35.2 | 68.9 | 4.6 | 26.5 | 100 | 21.2 | 0.5 |
| 31 | 0.50 | 29.0 | 36.2 | 70.2 | 4.1 | 25.6 | 100 | 21.4 | 0.5 |
| 18 | 1.00 | 28.7 | 34.9 | 69.0 | 4.8 | 26.2 | 100 | 20.9 | 0.6 |

TABLE 4-continued

ACTIVITY AND SELECTIVITY OF MIXTURES OF SrO AND $La_2O_3$
FOR THE CONVERSION OF METHANE AT 750° C.

| Example | SrO (wt %) | Selectivity (%) | | | | | Conversion (%) | | $H_2/(C_2H_4 + C_2H_6)$ |
|---|---|---|---|---|---|---|---|---|---|
| | | $C_2H_4$ | $C_2H_6$ | All $C_n$ | CO | $CO_2$ | $O_2$ | $CH_4$ | |
| 32 | 2.00 | 28.9 | 35.8 | 69.9 | 5.1 | 25.0 | 100 | 21.0 | 0.5 |
| 33 | 10.00 | 28.0 | 35.2 | 67.6 | 3.4 | 29.0 | 100 | 20.6 | 0.5 |

Comparison of the data in Table 4 indicates that the weight loading of the promoter oxide is not critical. An increase in selectivity to higher hydrocarbons of 10 percentage points is achieved by depositing SrO onto $La_2O_3$, irrespective of whether the weight loading of strontium oxide is 0.25% or 10.0%.

EXAMPLE 35-38

This example illustrates the use of rare earth oxide mixtures as catalysts for the conversion coupling of methane, wherein the mixture is obtained from the mineral ore, and a portion of the cerium has been removed.

Bastnasite ore was obtained and dissolved in an acidic solution. From this solution varying levels of cerium was removed by extraction. The lanthanide concentrate was then converted into a rare earth carbonate, filtered, and dried. The carbonate was subsequently decomposed to the oxide by calcining in air at 750° C. for 4 hours. Pure cerium oxide was also obtained for comparison with the rare earth oxide mixtures. The catalysts prepared are listed in Table 5. The amount of $La_2O_3$, $CeO_2$, and other rare earth oxides contained in each catalyst is given in the Table.

EXAMPLE 39

This example describes the test procedure for the evaluation of the rare earth oxide mixtures prepared in Examples 35-38, and sets forth the results.

Each of the catalysts of Examples 35-38 were separately pressed into pellets of mesh size between 20 and 32, charged to the quartz reactor, and exposed to the reaction conditions as described in Example 12 above. The experimental results for these catalyst samples are given in Table 5.

A comparison of the data in Table 5 indicates that a decrease in the selectivity to higher hydrocarbons occurs as the $CeO_2$ content of the rare earth oxide increases. Mixtures containing up to 10 wt % $CeO_2$ give acceptable results. However, at higher concentrations of cerium the selectivity decreases to a low value, and pure $CeO_2$ converts essentially all of the methane to carbon oxides.

EXAMPLE 40

This example compares two catalysts according to the present invention with a prior art catalyst consisting of lead oxide supported on silica.

A lead oxide on silica catalyst was prepared according to the procedure given by W. Hinsen, W. Bytyn, and M. Baerns, Proc. 8th Intl. Cong. Catal. 3, 581 (1984). Cab-O-Sil HS5 silica was impregnated to incipient-wetness by a solution of lead acetate dissolved in distilled water. The mixture was dried in a vacuum oven at 120° C. for 12 hours. The dried solid was then calcined in air at 800° C. for 4 hours. Enough lead was deposited on the $SiO_2$ to give a finished loading of 11.2 wt % PbO.

The supported lead oxide catalyst was pressed into pellets of mesh size between 20 and 32, charged to the quartz reactor, and exposed to the reactor conditions as described in Example 12. The experimental results for this catalyst and for the catalysts of Examples 6 and 18 are given in Table 6.

TABLE 6

ACTIVITY AND MAXIMUM SELECTIVITY OF
PRIOR ART CATALYST FOR THE CONVERSION OF METHANE

| Example | Catalyst | T (°C.) | Selectivity (%) | | | | | Conversion (%) | | $H_2/(C_2H_4 + C_2H_6)$ |
|---|---|---|---|---|---|---|---|---|---|---|
| | | | $C_2H_4$ | $C_2H_6$ | All $C_n$ | CO | $CO_2$ | $O_2$ | $CH_4$ | |
| 40 | $PbO/SiO_2$ | 900 | 27.0 | 31.1 | 60.0 | 11.8 | 28.2 | 50 | 8.5 | 0.2 |
| 6 | $La_2O_3$ | 750 | 25.7 | 30.9 | 59.1 | 8.1 | 32.8 | 100 | 19.6 | 1.1 |
| 18 | $SrO/La_2O_3$ | 750 | 28.7 | 34.9 | 69.0 | 4.8 | 26.2 | 100 | 20.9 | 0.6 |

Although the 11.2% $PbO/SiO_2$ prior art catalyst exhibits selectivities to higher hydrocarbons similar to that of the catalysts disclosed in this invention, the activity of the prior art catalyst is low. For a reaction temperature of 900° C., only 50% of the oxygen is converted per pass. For the $La_2O_3$ and $SrO/La_2O_3$ catalysts, on the other hand, 100% of the oxygen is converted per pass at temperatures as low as 600° C. Also, a comparison of the data shown in Table 6 indicates that the relative amount of hydrogen produced by PbO/-

TABLE 5

ACTIVITY AND SELECTIVITY OF RARE EARTH OXIDE MIXTURES
FOR THE CONVERSION OF METHANE AT 750° C.

| Example | Oxide Composition (%) | | | Selectivity (%) | | | | | Conversion (%) | | $H_2/(C_2H_4 + C_2H_6)$ |
|---|---|---|---|---|---|---|---|---|---|---|---|
| | $La_2O_3$ | $CeO_2$ | $Re_2O_3$ | $C_2H_4$ | $C_2H_6$ | All $C_n$ | CO | $CO_2$ | $O_2$ | $CH_4$ | |
| 6 | 100 | 0 | 0 | 25.7 | 30.9 | 59.1 | 8.1 | 32.8 | 100 | 19.6 | 1.1 |
| 35 | 67 | 1 | 32 | 17.8 | 30.0 | 49.8 | 8.7 | 41.5 | 100 | 16.5 | 1.0 |
| 36 | 60 | 10 | 30 | 18.4 | 31.8 | 52.2 | 3.8 | 44.0 | 100 | 15.5 | 0.5 |
| 37 | 40 | 40 | 20 | 7.9 | 16.2 | 24.5 | 8.7 | 66.8 | 100 | 11.6 | 2.2 |
| 38 | 0 | 100 | 0 | 0.3 | 1.6 | 2.0 | 9.3 | 88.7 | 100 | 9.3 | 32.9 |

$SiO_2$ is much less than that produced by either $La_2O_3$ or $SrO/La_2O_3$. Thus, the catalysts disclosed in the present invention are superior to the prior art catalyst for the synthesis of hydrocarbons from methane in the presence of oxygen.

It is understood that the foregoing detailed description is given merely by way of illustration and that many variations may be made therein without departing from the spirit of this invention.

What is claimed is:

1. A catalyst for converting methane in the presence of oxygen into higher hydrocarbon products consisting essentially of
   (1) a base metal oxide where the metal is selected from the group consisting of metals of
     (a) Group IIA metals of the Periodic Table excluding Mg, which are Be, Ca, Sr, Ba and mixtures thereof; and
     (b) Sc, Y, rare earth metals of the Periodic Table excluding Ce, Pr and Tb, which are La, Nd, Sm, Eu, Gd, Dy, Ho, Er, Tm, Yb, and Lu and mixtures thereof; and
   (2) a promoter oxide present in an amount of up to 50 wt % of the mixture where the metal is selected from the group consisting of
     (a) Group IA metals of the Periodic Table, which are Li, Na, and K provided that the base metal oxide is not just selected from (1)(a) alone;
     (b) Group IIA metals of the Periodic Table excluding Mg, which are Be, Ca, Sr, and Ba provided that base metal oxide is not just selected from (1)(a) alone;
     (c) Sc, Y, and rare earth metals of the Periodic Table excluding Ce, Pr and Tb, which are La, Nd, Sm, Eu, Gd, dy, Ho, Er, Tm, Yb, and Lu, provided that the base metal oxide is not just selected from (1)(b) alone; and
     (d) mixtures thereof.

2. A catalyst according to claim 1, wherein the promoter oxide is present in an amount up to 10 wt % of the mixture.

3. A catalyst according to claim 1, wherein the base metal oxide is $Y_2O_3$ and the promoter oxide is $Li_2O$, BeO, CaO, SrO, or BaO.

4. A catalyst according to claim 1, wherein the base metal oxide is $La_2O_3$ and the promoter oxide is $Li_2O$, BeO, CaO, SrO, or BaO.

5. A catalyst for converting methane in the presence of oxygen into higher hydrocarbon products consisting essentially of as the sole catalytic component a base metal oxide in the form of a mixture of rare earth oxides, as is formed in rear earth minerals, but with a poriton of $CeO_2$ removed, and a promoter oxide of $Li_2O$, BeO, CaO, SrO, or BaO.

6. Aa catalyst according to claim 1, wherein the promoter oxide is deposited onto the base metal oxide.

* * * * *

UNITED STATES PATENT AND TRADEMARK OFFICE
CERTIFICATE OF CORRECTION

PATENT NO. : 4,780,449

DATED : October 25, 1988

INVENTOR(S) : Robert F. Hicks

It is certified that error appears in the above-identified patent and that said Letters Patent is hereby corrected as shown below:

In Claim 1, part (2)(c), line 3, change "dy" to --Dy--.

In Claim 5, line 5, change "rear" to --rare-- and "poriton" to --portion--.

In Claim 6, line 1, change "Aa" to --A--.

Signed and Sealed this

Seventh Day of March, 1989

Attest:

DONALD J. QUIGG

Attesting Officer

Commissioner of Patents and Trademarks